United States Patent
Fox et al.

(10) Patent No.: US 6,897,324 B2
(45) Date of Patent: May 24, 2005

(54) PROCESS FOR THE PREPARATION OF 11-OXAPROSTAGLANDINS AND INTERMEDIATES THEREIN

(75) Inventors: Martin Edward Fox, Histon (GB); Mark Jackson, Cambridge (GB)

(73) Assignee: Chirotech Technology Limited (GB)

( * ) Notice: Subject to any disclaimer, the term of this patent is extended or adjusted under 35 U.S.C. 154(b) by 347 days.

(21) Appl. No.: 10/276,846

(22) PCT Filed: May 16, 2001

(86) PCT No.: PCT/GB01/02184
§ 371 (c)(1),
(2), (4) Date: May 5, 2003

(87) PCT Pub. No.: WO01/87897
PCT Pub. Date: Nov. 22, 2001

(65) Prior Publication Data
US 2003/0166948 A1 Sep. 4, 2003

(51) Int. Cl.⁷ ............................................. C07D 307/20
(52) U.S. Cl. .................. 549/313; 549/214; 549/475; 549/478; 549/497
(58) Field of Search ................. 549/313, 214, 549/475, 478, 497

(56) References Cited

FOREIGN PATENT DOCUMENTS

EP          0 299 914 A    *  1/1989
WO          90/02553       *  3/1990

* cited by examiner

*Primary Examiner*—Ba K. Trinh

(57) ABSTRACT

For the preparation of an 11-oxaprostaglandin such as [2R,(1E,3R),3S,(4Z),4R)]-7-{tetrahydro-2-[4-(3-chlorophenoxy)-3-hydroxy-1-butenyl]-4-hydroxy-3-furanyl}-4-heptenoic acid and its ester derivatives, a novel process uses a novel enantiomerically enriched compound for formula (1) wherein the bond between carbon atoms y and z is either a single or double bond; $R^1$ is selected from vinyl, trialkylsilylethynyl, a formyl group protected as an acetal, or a protected hydroxymethyl group; $R^2$ is $C_{1-5}$ alkyl, optionally substituted at the terminus with an aryloxy or alkoxy group; and $R^3$–$R^6$ are independently selected from $C_{1-6}$ alkyl and $C_{6-10}$ aryl

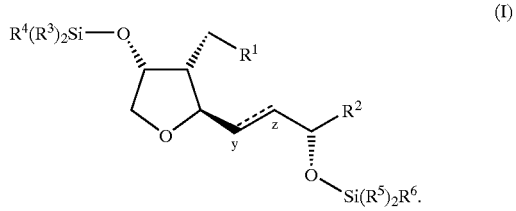

19 Claims, No Drawings

PROCESS FOR THE PREPARATION OF 11-OXAPROSTAGLANDINS AND INTERMEDIATES THEREIN

This application is a 371 of PCT/GB01/02184 filed May 16, 2001.

FIELD OF THE INVENTION

This invention relates to the preparation of 11-oxaprostaglandins and to intermediates in that process.

BACKGROUND OF THE INVENTION

11-Oxaprostaglandins, in particular [2R, (1E, 3R), 3S, (4Z), 4R)]-7-{tetrahydro-2-[4-(3-chlorophenoxy)-3-hydroxy-1-butenyl]-4-hydroxy-3-furanyl}-4-heptenoic acid and its ester derivatives, in particular the isopropyl ester (i), are potent drugs for the treatment of glaucoma and ocular hypertension. Optimum therapeutic benefit is achieved when compound (i) is used in the form of the dextrorotatory single enantiomer (+)-i. For development as a pharmaceutical product, an economically viable route is required for the synthesis of (+)-i in quantities of at least 1 kg. The structure of (+)-i is shown below.

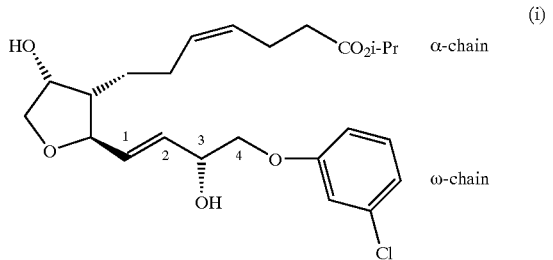

Previous routes to 11-oxaprostaglandins employ a $C_1$–$C_2$ olefination reaction of a tetrahydrofuran-2-carboxaldehyde for the introduction of the ω-chain. The α-chain may be introduced before or after this step. The tetrahydrofuran-2-carboxaldehyde may be prepared from several readily available carbohydrates, which provide the four carbons of the tetrahydrofuran core and C1 of the ω-chain. The following carbohydrates have been used as starting materials in this approach: D-sorbitol (J. Thiem and H. Lü ders, *Liebigs. Ann. Chem.*, 1985, 2151, and S. Hanessian et al, *Carbohydrate Research*, 1985, 141, 221), D-xylose and D-glucose (G. J. Lourens and J. M. Koekemoer, *Tetrahedron Lett*, 1975, 43, 3719 and R. R. Arndt et al, *S.-Afr. Tydskr. Chem.*, 1981, 34, 121).

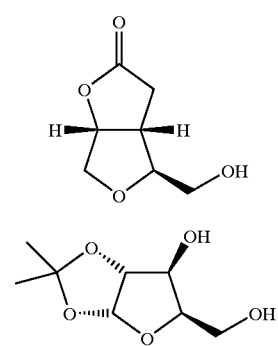

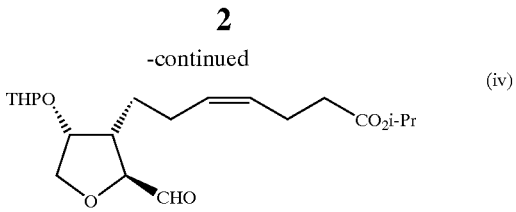

WO-A-97/23223 discloses the synthesis of (+)-i from (3aR, 4S, 6aR)-4-hydroxymethylhexahydrofuro[3,4-b]furan-2-one (ii). The latter is prepared from 1,2-O-isopropylidene-α-D-xylofuranose (iii) in 9 steps. The α-chain of the prostaglandin is introduced first. After protection of the hydroxyl group as a tert-butyldiphenylsilyl ether, the lactone is reduced to the lactol, then a 1-carbon Wittig homologation followed by a Z-selective Wittig reaction-completes assembly of the α-chain. The ring hydroxyl group is protected as a tetrahydropyranyl ether, then the silyl protecting group is removed. Oxidation of the liberated hydroxyl group provides the tetrahydrofuran-2-carboxaldehyde intermediate (iv). E-Selective Horner-Wadsworth-Emmons reaction with dimethyl 2-oxo-3-(3-chlorophenoxy)propylphosphonate introduces C2–C4 of the ω-chain, after which non-stereoselective reduction of the enone followed by removal of the tetrahydropyranyl group completes the synthesis of (i), but the product is contaminated with the unwanted 3Sepimer. The active 3R diastereoisomer is obtained by chromatographic separation.

This synthetic approach to (+)-i has a number of limitations, including the following, that preclude its use for commercial manufacturing purposes.

1. The synthesis is linear, requiring a large number of sequential steps [20 steps from starting material (iii)].
2. Construction of the α-side chain is cumbersome, requiring two Wittig reactions to effect 1-carbon and 4-carbon homologation.
3. Reduction of the C3 carbonyl group is unselective and requires chromatographic separation of the unwanted 3S epimer at the end of the synthesis.

An alternative and more convergent approach to prostaglandins involves addition of a cuprate reagent, incorporating the entire ω-side chain, to an electrophilic core synthon. This approach has been extensively used for carbocyclic prostaglandins, where the core synthon may be a tricyclo [3.2.0.0$^{2,7}$]heptanone (Lee et al, *J. Chem. Soc., Perkin Trans* 1, 1978, 1176) or a cyclopentenone (G Stork and M Isobe, *J. Am. Chem. Soc.*, 1975, 97, 6260; H Tsujiyama et al, *Tetrahedron Lett.*, 1990, 31, 4481; J W Patterson and J H Fried, *J. Org. Chem.*, 1974, 39, 2506; R Noyori, 'Asymmetric Catalysis in Organic Synthesis', Chapter 6, Wiley Interscience, New York, 1994). Hitherto this approach has not been used in the synthesis of 11-oxaprostaglandins.

A. S. Thompson et al, *J. Org. Chem.*, 1992, 57, 7044, disclose the preparation of trans-2,5-diaryltetrahydrofurans by coupling of aryl Grignard reagents, optionally in the presence of a copper catalyst, to 2-hydroxy-5-aryltetrahydrofurans prepared by reduction of the 5-aryltetrahydrofuran-2-ones. As depicted in Scheme 1, below, this entails an activation procedure in which the 2-hydroxytetrahydrofuran is converted to a 2-bromotetrahydrofuran by silylation followed by reaction with trimethylsilyl bromide at low temperature. It is likely that an $S_n1$-type mechanism operates in the subsequent formation of the carbon—carbon bond, involving ionisation of the 2-bromotetrahydrofuran to form a mesomerically stabilised oxacarbenium ion as the reactive species. Broader applications of this methodology, e.g. to introduce non-aromatic groups to a tetrahydrofuran nucleus, have hitherto not been reported.

O. Muraoka et al, *J. Chem. Soc. Perkin Trans.* 1, 1994, 1833, disclose the preparation of cis-4-hydroxy-3-alkyl-tetrahydrofuran-2-ones by stereoselective alkylation of methyl (4-tert-butylsilyldimethyloxy)-3-hydroxybutanoate followed by lactonisation under acidic conditions.

SUMMARY OF THE INVENTION

The present invention allows the preparation of enantiomerically enriched 11-oxaprostaglandins by means of a novel coupling reaction, providing a shorter and more convergent synthesis than previous routes. This invention is based on the discovery of a stereoselective process for coupling an omega-side chain cuprate reagent to a 2-hydroxytetrahydrofuran core synthon, giving overall a particularly effective synthesis of 11-oxaprostaglandin agents, in particular [2R, (1E, 3R), 3S, (4Z), 4R)]-7-{tetrahydro-2-[4-(3-chlorophenoxy)-3-hydroxy-1-butenyl]-4-hydroxy-3-furanyl}-4-heptenoic acid and its ester derivatives, e.g. (+)-i.

The stereoselective coupling reaction provides a novel trisubstituted tetrahydrofuran of the formula (1):

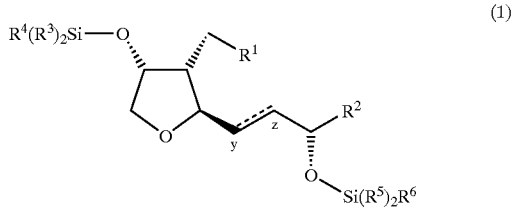
(1)

wherein the bond between between carbon atoms y and z is either a single or double bond; $R^1$ is selected from vinyl, trialkylsilylethynyl, a formyl group protected as an acetal, or a protected hydroxymethyl group; $R^2$ is $C_{1-5}$ alkyl, optionally substituted at the terminus with an aryloxy or alkoxy group; and $R^3$–$R^6$ are independently selected from $C_{1-6}$ alkyl or $C_{6-10}$ aryl.

The silyl acetals 2 and lactones 5 shown below are also new compounds, according to the invention, in enantiomerically enriched form. A novel compound is typically in an enantiomeric excess (ee) of at least 90%, preferably at least 95%.

DESCRIPTION OF THE INVENTION

Since it is essentially a spectator group, the nature of $R^1$ is not critical, provided that it contains no incompatible functionality such as a base-sensitive group. Preferably, $R^1$ is a two-carbon unit selected from vinyl and trialkylsilylethynyl and is more preferably vinyl. The trisubstituted tetrahydrofuran (1) may be readily converted to the target 11-oxaprostaglandin using conventional processes.

The novel coupling process comprises sequential reaction of a silyl acetal of formula 2, wherein $R^7$ is $C_{1-6}$n-allyl, with a trimethylsilyl halide TMS-Y, wherein the halide Y is either bromide or iodide to form the intermediate 2-halotetrahydrofuran 3, and an organometallic derivative of an alkenyl or alkyl halide of formula 4, wherein X is a halide. Typically, an alkenyl halide (more preferably an alkenyl iodide) is used, and the organometallic derivative is a cuprate reagent.

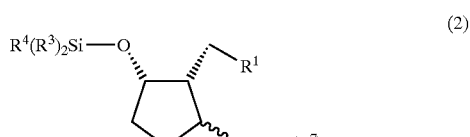

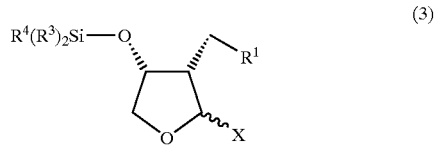

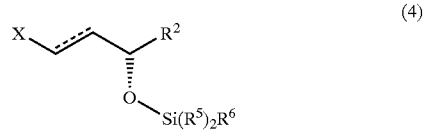

The silyl acetal 3 is prepared by reduction of a lactone of formula 5 followed by silylation of the resultant lactol. In a preferred embodiment of the present invention, the enantiomerically enriched lactone 5 wherein $R^1$ is vinyl, $R^3$ is methyl and $R^4$ is tert-butyl was found unexpectedly to be crystalline, thereby allowing its isolation in diastereomerically pure form without resort to column chromatography. This lactone may be used for the preparation of 11-oxaprostaglandins containing a either a 4- or 5-heptenoate α-chain, by transformation of the vinyl group by ozonolysis and hydroboration respectively.

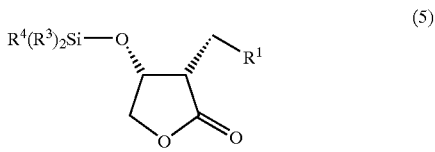

The lactone 5 is prepared by methods analogous to those of Muraoka et al, supra, from methyl (R)-4-(tert-butyldimethylsilyloxy)-3-hydroxybutanoate, by stereoselective alkylation with an alkylating agent $R^1$—$CH_2X$ wherein X is a leaving group, which may be bromide, iodide or sulphonate followed by cyclisation to the hydroxy furanone and protection with a silyl group. Methyl (R)-4-(tert-butyldimethylsilyloxy)-3-hydroxybutanoate is readily prepared from inexpensive D-malic acid.

The omega side-chain component 4, wherein carbon atoms x and y are connected by a double bond, is prepared in enantiomerically enriched form by methods such as those disclosed in WO-A-95/33845 and WO-A-00/61777.

Scheme II summarises the novel process chemistry embodied by the present invention, culminating in coupling of the alkenylcuprate reagent 6 to the silyl acetal 3 to provide the trisubstituted tetrahydrofuran 1a. All reactants depicted are used in enantiomerically enriched form, typically in >95% ee or higher.

Step (i) is the preparation of the lactol 7. This is achieved by treatment of the lactone 5 with a reducing agent in an appropriate solvent, preferably diisobutylaluminium hydride in toluene. The lactol 7 is used without purification in step (ii).

Step (ii) is the formation of the silyl acetal 2 from the lactol 7 by silylation. The preferred trialkylsilyl group is trimethylsilyl, conveniently introduced by reaction of the lactol with trimethylsilyl chloride and triethylamine. This preference is based on the observation that bulkier trialkylsilyl groups, e.g. TBDMS, can result in the formation of significant amounts of a ring-opened by-product, the silylated hydroxyaldehyde 8 wherein $(R^7)_3$=tert-butyldimethyl. A similar observation has been reported in silylation of lactol intermediates in the synthesis of nucleoside analogues (E. K. Yau and J. K. Coward, *J. Org. Chem.*, 1990, 55, 3147).

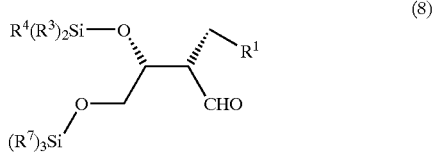

(8)

Step (iii) is the activation of the silyl acetal 2 to the 2-halotetrahydrofuran 3 (Y=Br, I). This is achieved by reaction with a silyl halide, preferably trimethylsilyl bromide. The activation is carried out at a temperature below −30° C. and the 2-halotetrahydrofuran 4 is used directly in step (v) without allowing the temperature to rise above −30° C.

Step (iv) is the formation of an alkenylcuprate reagent 6 from the vinyl iodide 4a. The vinyl iodide is metallated with an alkyllithium reagent, preferably tert-butyllithium, and then treated with a cuprate of the form RCu(CN)Li where R is a non-transferable group which may be 2-thienyl.

Step (v) is the stereoselective reaction of the alkenylcuprate 6 with the 2-halotetrahydrofuran 7 to form the trisubstituted tetrahydrofuran 1a. After isolation and purification, this pivotal intermediate can be obtained in good yield as an analytically pure single stereoisomer. Thus the correct absolute and relative configuration across four chiral centres, also present in the final target prostaglandin, is established in this step. In the context of related work by Thompson et al. (Scheme I), several novel and inventive features of this reaction can be identified:

1. Introduction of a non-aromatic hydrocarbon substitutent at the 2-position of the tetrahydrofuran ring, by reaction of the corresponding 2-silyloxytetrahydrofuran with an organometallic nucleophile, is demonstrated for the first time.
2. In contrast to the work of Thompson et al., stereocontrol at the 2-position of the tetrahydrofuran ring appears to derive from one or both substituents at 3- and 4-positions, rather than one at the 5-position. However, it would have been difficult to predict the observed stereoselectivity, since subtle stereoelectronic effects can operate in the reaction of nucleophiles in five-membered-ring oxacarbenium ions (C. H. Larsen, B. H. Ridgeway, J. T. Jared and K. A. Woerpel, *J. Am. Chem. Soc.*, 1999, 121, 12208).
3. For introduction of an alkenyl or alkyl substituent at the 2-position of the tetrahydrofuran ring, it is preferable to use an organocuprate reagent rather than a Grignard reagent.
4. Highly functionalised substituents may be introduced. For example, in the synthesis of the the alkenyl cuprate reagent required for the 11-oxaprostaglandin (i), reaction with excess tert-butyl lithium gives highly selective metallation of the vinyl iodide group and the aryl-chloride group is unaffected.

Scheme III summarises a specific embodiment of the present invention, the conversion of trisubstituted tetrahydrofuran 9 wherein $R^1$ is vinyl, $R^2$ is 3-chlorophenoxymethyl, $R^3$ and $R^5$ are methyl, $R^4$ and $R^6$ are tert-butyl and y-z is a (E)-double bond to the 11-oxaprostaglandin isopropyl [2R,(1E,3R),3S,(4Z),4R)]-7-{tetrahydro-2-[4-(3-chlorophenoxy)-3-hydroxy-1-butenyl]-4-hydroxy-3-furanyl}-4-heptenoate (+)-i. Each step involves conventional methodology.

Step (i) is hydroboration of the double bond of the allyl substituent to a primary alcohol with a borane which may be 9-borabicyclo[3.3.1]nonane.

Step (ii) is oxidation of the primary alcohol to the aldehyde 10, which may be effected in high yield under Swern conditions.

Step (iii) is a Wittig reaction with the ylide generated from (3-isopropoxycarbonylpropyl)triphenylphosphonium bromide and potassium tert-butoxide or potassium bis(trimethylsilyl)amide.

Step (iv) is the removal of the silyl protecting groups with tetra n-butylammonium fluoride to give the 11-oxaprostaglandin (+)-i.

The following Examples illustrate the invention.
MTBE is methyl tert-butyl ether.

EXAMPLE 1

Methyl (2S,3R)-4-(tert-butyldimethylsilyloxy)-3-Hydroxy-2-(1-trimethylsilylpropargyl)butanoate n-Butyllithium (2.5M, 17.7 ml, 44.3 mmol) was added dropwise to a solution of diisopropylamine (6.75 ml, 48.3 mmol) in tetrahydrofuran (40 ml) at −10° C. under nitrogen (exothermic, temperature maintained at 0 to −5° C. with external cooling). The solution was stirred at 0° C. for 10 minutes and then cooled to −50° C. A solution of methyl (R)-(4-tert-butylsilyldimethyloxy)-3-hydroxybutanoate (5.0 g, 20.1 mmol) in tetrahydrofuran (10 ml) was added over 5 minutes and residual ester was washed in with further tetrahydrofuran (5 ml) (the addition was exothermic, causing the internal temperature to rise to −35° C.). The cold bath was removed and the reaction allowed to warm to −10° C. After 10 minutes, the mixture was recooled to −50° C. 1,3-Dimethyl-2-imidazolidinone (2.81 ml, 26.2 mmol) was added and after stirring for 5 minutes, trimethylsilylpropargyl bromide (4.7 ml, 30.2 mmol) in tetrahydrofuran (15 ml) was added (immediate colour change from yellow to dark brown) and the reaction was allowed to warm to room temperature over 3 h (TLC MTBE/heptane 1:3 showed no starting material). The reaction was quenched with saturated ammonium chloride (100 ml). The organic layer was separated and the aqueous phase was extracted with MTBE (100 ml). The combined organic phases were washed with water (50 ml) and brine (50 ml), dried (MgSO$_4$), filtered and evaporated. The crude product was chromatographed (MTBE/heptane 1:4) to give the title compound as a light brown liquid (3.95 g, 11.0 mmol, 55%); $v_{max}$ (film) 3508, 2178 and 1738 cm$^{-1}$; $^1$H NMR (200 MHz, CDCl$_3$) δ ppm 3.94–3.88 (1 H, m), 3.72 (3 H, s), 3.70–3.67 (2 H, m), 2.98 (1 H, d, J 7), 2.82–2.75 (1 H, m), 2.61–2.58 (2 H, m), 0.90 (9 H, s), 0.11 (9 H, s) and 0.08 (6 H, s); m/z (GCMS, EI) 301 (M-$^t$Bu, 4%) and 117 (100).

EXAMPLE 2

(3S,4R)-4-hydroxy-3-(1-trimethylsilylpropargyl)tetrahydrofuran-2-one

The hydroxyester of Example 1 (4.2 g, 11.7 mmol) was dissolved in 1,2-dimethoxyethane (40 ml). Aqueous hydrochloric acid (2N, 20 ml) was added and the mixture was heated at 80° C. for 75 minutes (TLC MTBE/heptane 3:1 showed complete reaction). After cooling to room temperature, the mixture was extracted with MTBE (2 ×30 ml). The combined organic extracts were washed with saturated sodium hydrogencarbonate solution (30 ml) and brine (30 ml), dried MgSO$_4$), filtered and evaporated. Heptane (10 ml) was added to the oily residue and the mixture was cooled in an ice bath. The crystalline solid was filtered, washed with heptane (2 ml) and dried to give the lactone (1.59 g, 7.5 mmol, 64%); m.p. 75° C. (onset by DSC); v$_{max}$ (Nujol) 3434, 2175 and 1768 cm$^{-1}$; $^1$H NMR (200 MHz, CDCl$_3$) δ ppm 4.75 (1 H, br), 4.38 (2 H, m), 2.90–2.77 (2 H, m), 2.60 (1 H, dd, J 18, 12), 2.46 (1 H, br) and 0.13 (9 H. s); m/z (GCMS, EI) 179 (100%).

EXAMPLE 3

(3S,4R)-4-(ter-Butyldimethylsilyloxy)-3-(1-trimethylsilylpropargyl)-tetrahydrofuran-2-one The hydroxy lactone of Example 2 (1.57 g, 7.39 mmol) was dissolved in dry dimethylformamide (4 ml) under nitrogen. Imidazole (755 mg, 11.1 mmol) and then tert-butyldimethylsilyl chloride (1.33 g, 8.9 mmol) were added and the mixture was stirred at room temperature overnight (TLC MTBE/heptane 1:3 showed complete reaction). The mixture was partitioned between water (20 ml) and heptane (2×30 ml) and the combined organic phases were dried (MgSO$_4$). The solvent was evaporated and the residue was passed through a short silica column eluting with MTBE/heptane 1:8 to give the lactone (2.28 g, 7.0 mmol, 94%); m.p. 66° C. (onset by DSC); v$_{max}$(Nujol) 2179 and 1765 cm$^{-1}$; $^1$H NMR (200 MHz, CDCl$_3$) δ ppm 4.63 (1 H, t, J 3.5), 4.30 (1 H, dd, J 10, 3), 4.20 (1H, d, J 10), 2.78–2.67(2 H, m), 2.52(1H, dd, J 17, 12), 0.90(9 H, s), 0.15(9H, s) and 0.13 (6 H, s); m/z (GCMS, EI) 269 (M-$^t$Bu, 38%) and 117 (100).

EXAMPLE 4

(3S,4R)-4-(tert-butyldimethylsilyloxy)-3-(1-trimethylsilylpropargyl)-tetrahydrofuran-2-ol The lactone of Example 3 (680 mg, 2.1 mmol) was dissolved in dry toluene (7 ml) and cooled to –70° C. under nitrogen. Diisobutylaluminium hydride (1.5M, 2.0 ml, 3.0 mmol) was added dropwise and the resulting mixture was stirred for 3 h. The reaction was quenched with methanol (1 ml) (vigorous frothing initially). Aqueous sulfuric acid (2 N, 10 ml) was added and the mixture was allowed to warm to room temperature. The organic layer was separated and the aqueous phase was extracted with MTBE (2×15 ml). The combined organic solutions were washed with aqueous sulfuric acid (2N, 10 Ml), water (3×10 ml, to pH 7) and brine (10 ml). The solution was dried (MgSO$_4$), filtered and evaporated to give the lactol as a colourless oil (680 mg, 99%), 2:1 mixture of anomers; $^1$H NMR (200 MHz, CDCl$_3$) δ ppm 5.28 (1 H, t, J 4, major), 5.19 (1 H, dd, J 12, 4.5, minor), 4.50 (1 H, m, major), 4.42 (1 H, t, J 3.5, minor), 4.18–4.04 (1 H, m, both anomers), 3.94 (1 H, dd, J 10, 3, minor), 3.75–3.63 (1 H, m, both anomers), 2.98 (1 H, d, J 4, major), 2.57–2.15 (3 H, m, both anomers), 0.90 (9 H, s, both anomers) and 0.16–0.07 (15 H, m, both anomers).

EXAMPLE 5

(3S,4R)-4-(tert-butyldimethylsilyloxy)-2-trimethylsilyloxy-3-(1-trimethylsilylpropargyl) tetrahydrofuran The lactol of Example 4 (215 mg, 0.65 mmol) was dissolved in dry tetrahydrofuran (2 ml) at room temperature under nitrogen. Triethylamine (0.14 ml, 1.0 mmol) and then trimethylsilyl chloride (0.10 ml, 0.78 mmol) were added and the mixture was stirred for 1 h. The reaction was partitioned between heptane (20 ml) and water (10 ml). The heptane layer was washed with brine (10 ml), dried (MgSO$_4$), filtered and evaporated to give the silyl acetal as a colourless oil (241 mg, 0.60 mmol, 93%), approx 4:1 mixture of anomers; $^1$H NMR (200 MHz, CDCl$_3$) δ ppm (major anomer) 5.29 (1 H, d, J 3), 4.50 (1 H, m), 4.09 (1 H, dd, J 9, 5), 3.61 (1 H, dd, J 9, 3), 2.50–2.42(1 H, m), 2.30–2.15 (2 H, m), 0.90 (9 H, s) and 0.10 (24 H, m).

EXAMPLE 6

4-(tert-butyldimethylsilyloxy)-2-[3-(tert-butyldimethylsilyloxy)-4-(3-chlorophenoxy)but-1-enyl]-3-(3-trimethylsilylprop-2-ynyl)tetrahydrofuran The silyl acetal of Example 5 (560 mg, 1.4 mmol) was dissolved in dry dichloromethane (51 ml) and cooled to –50° C. under nitrogen. Trimethylsilyl bromide (0.18 ml, 1.4 mmol) was added and the mixture was stirred for 1.5 h, maintaining the temperature at –40 to –50° C.

A solution of racemic vinyl iodide iodide (E)-1-iodo4-(3-chlorophenoxy)-3-tert-butyldimethylsilyloxy-1-butene (797 mg, 1.8 mmol) in ether (5 ml) was added dropwise to tert-butyllithium (1.5M 2.25 rnl) at –78° C. under nitrogen The solution was stirred for a further 50 minutes.

n-Butyllithium (2.5 M, 0.73 ml, 1.8 mmol) was added to thiophene (153 mg, 1.8 mmol) in dry tetrahydrofuran (1 ml) at –20° C. under nitrogen. The thienyllithium solution was stirred for 15 minutes and then added to a suspension of copper cyanide (163 mg, 1.8 mmol) in tetrahydrofuran (1 ml) at –20° C under nitrogen [residues were washed in with tetrahydrofuran (0.5 ml)]. The mixture was allowed to warm to room temperature (a clear brown solution was obtained). The lithium 2-thienylcyanocuprate solution was added to the vinyllithium solution, washing in with tetrahydrofuran (0.5 ml). After 5 minutes, the activated bromoether solution was cooled to –70° C. and added to the cuprate, washing in with tetrahydrofuran (2 ml) (clear yellow solution resulted). After 75 minutes, TLC (5% MTBE in heptane) indicated complete reactions The reaction was quenched with saturated ammonium chloride solution (10 ml) and water (10 ml) and allowed to warm to room temperature. The mixture was extracted with MTBE (2×25 ml) and the combined organic phases were washed with brine (20 ml), dried MgSO$_4$), filtered and evaporated to give a brown oil (1.15 g). This was chromatographed (5% MTBE in heptane) to give a pale yellow oil (542 mg, 0.9 mmol, 62%); $^1$H NMR (400 MHz, CDCl$_3$) δ ppm 7.20 (1 H, t, J 8), 6.92 (1H, d, J 8), 6.89 (1H s), 6.79 (1H, d, J 8), 5.77 (2 H, m), 4.55 (1H, m), 4.47 (1H, m), 4.07 (2 H, m), 3.83 (2 H, m), 3.77 (1 H, m), 2.41 (1H, m), 2.15 (1 H, dt, J 16, 4), 1.95 (1 H, m), 0.92 (18 H, s) and 0.15–0.07 (21 H, m); $^{13}$C NMR (100 MHz, CDCl$_3$) δ ppm (values in parentheses attributed to pair of diastereomers) 159.51, 134.81, 132.60, (131.15 and 130.98), 130.17, 120.90, 114.91, 112.96, 105.63, 84.98, 81.70, 75.61, 72.93, (72.41 and 72.26), 71.17, (50.78 and 50.72), 25.82, 18.32, 18.07, 15.73, (0.09 and 0.00), –4.56, –4.61, –4.68 and –5.00.

EXAMPLE 7

Methyl (2S,3R)-2-Allyl-4-(tert-butyldimethylsilyloxy)-3-hydroxybutanoate n-Butyllithium (2.5M 51.2 ml, 127.9 mmol) was added dropwise to a solution of diisopropylamine (19.5 ml, 139.5 mmol) in tetrahydrofuran (100 ml) at 0° C. under nitrogen (exothermic, temperature maintained at 0 to −5° C. with external cooling). The solution was stirred at 0° C. for 10 minutes and then cooled to −60° C. A solution of methyl (R)-(4-tert-butylsilyldimethyloxy)-3-hydroxybutanoate (14.44 g, 58.1 mmol) in tetrahydrofuran (30 ml) was added and residual ester was washed in with further tetrahydrofuran (10 ml) (the addition was exothermic causing the internal temperature to rise to −47° C.). The cold bath was removed and the reaction allowed to warm to 0° C. The mixture was then recooled to −60° C. 1,3-Dimethyl-2-imidazolidinone (8.2 ml, 75.6 mmol) was added and after stirring for 5 minutes, allyl bromide (7.4 ml, 87.2 mmol) was added. The mixture was stirred below −50° C. for 30 mins. The cold bath was removed and the reaction allowed to warm to 10° C. over 1 h (TLC MTBE/Heptane 1:3 showed no starting material). The reaction was quenched with saturated ammonium chloride (150 ml) (internal temperature rose to 23° C.). The organic layer was separated and the aqueous phase was extracted with MTBE (100 ml). The combined organic phases were washed with brine (100 ml), dried ($MgSO_4$), filtered and evaporated. The crude product was passed through a short silica column (100 g), eluting with MTBE/heptane 1:6 to give the title compound as a pale yellow liquid (13.85 g, 48.0 mmol, 82%); Found: C, 58.5; H, 9.8. $C_{14}H_{28}O_4Si$ requires C, 58.3; H9.8%; $v_{max}$(film) 3492, 1739 and 1642 $cm^{-1}$; [α] +6.5° (c=1.0, $CH_2Cl_2$); $^1$H NMR (400 MHz, $CDCl_3$) δ ppm 5.84–5.64 (1 H, m), 5.13–5.00 (2 H, m), 3.83–3.74 (1 H, m), 3.69 (3 H, s), 3.66–3.57 (2 H, m), 2.94 (1 H, d, J 7), 2.74–2.64 (1 H, m), 2.50–2.28 (2 H, m), 0.88 (9 H, s) and 0.05 (6 H, s); m/z (GCMS, EI) 231 (M-$^t$Bu, 16%) and 117 (100).

EXAMPLE 8

(3S,4R)-3-Allyl-4-hydroxytetrahydrofuran-2-one

The 2-allyl hydroxy ester of Example 7 (13.5 g, 46.8 mmol) was dissolved in 1,2-dimethoxyethane (100 ml). Aqueous hydrochloric acid (3N, 60 ml) was added and the mixture was heated at 80° C. for 1 h (TLC MTBE/heptane 4:1 showed complete reaction). After cooling to room temperature, the aqueous phase was saturated with sodium chloride and the mixture was extracted with ethyl acetate (3×70 ml). The combined organic extracts were dried ($MgSO_4$), filtered and evaporated. The crude product (10 g) was filtered through silica (35 g), eluting first with 30% MTBE in heptane (to remove silicon byproducts) and then with neat MTBE to afford the lactone (6.11 g, 43.0 mmol, 92%); $v_{max}$(film) 3444, 1759 and 1642 $cm^{-1}$;[α] +67.80° (c=1.0, $CH_2Cl_2$); $^1$H NMR (400 MFz, $CDCl_3$) δ ppm 5.90 (1 H, m), 5.25–5.10 (2 H, m), 4.55 (1 H, brs), 4.30 (2 H, m), 2.70–2.55 (3 H, m) and 2.50–2.40 (1 H, m); m/z (GCMS, EI) 123 (40%) and 79 (100).

EXAMPLE 9

(3S,4R)-3-Allyl-4-(tert-butyldimethylsilyloxy) Tetrahydrofuran-2-one

The hydroxy lactone of Example 8 (6.0 g, 42.2 mmol) was dissolved in dry dimethylformamide (10 ml) under nitrogen. Imidazole (4.78 g, 70.2 mmol) and then tert-butyldimethylsilyl chloride (7.05 g, 46.80 mmol) were added. The mixture was stirred at room temperature overnight and then partitioned between water (50 ml) and heptane (2×30 ml). The heptane extracts were dried ($MgSO_4$), filtered and evaporated to give the crude product (10.5 g). This was crystallised from heptane (40 ml) at −15° C. to give the title compound as a white solid (7.60 g, 29.6 mmol, 70%); m.p. 48° C. (onset by DSC); Found: C, 61.1; H, 9.5. $C_{13}H_{24}O_3Si$ requires C, 60.9; H, 9.4%; $v_{max}$ (Nujol) 1763 and 1644 $cm^{-1}$; [α] +88.0° (c=1.0, $CH_2Cl_2$); $^1$HNMR (400 MHz, $CDCl_3$) δ ppm5.94–5.80 (1 H, m), 5.18–5.06(2 H, m), 4.53 (1 H, t, J 3.5), 4.26 (1 H, dd, J 10,3), 4.17 (1 H, d, J 10), 2.60–2.35 (3 H, m), 0.89 (9 H, s), 0.10 (3 H, s) and 0.08 (3 H, s); m/z (GCMS, EI) 199 (M-$^t$Bu, 4%) and 117 (100).

The mother liquors were concentrated and observed to solidify upon standing. The solid was dissolved in heptane (25 ml) and cooled in a $CO_2$/acetone bath to induce crystallisation. The solid was filtered and washed with cold heptane (10 ml) to give a second crop of the lactone (646 mg, 2.5 mmol, 6%).

The residue was chromatographed (MTBE/heptane 1:6 to 1:3) to give
  i) the (3R, 4R) diastereomer as a colourless oil (456 mg, 1.8 mmol, 4%); $^1$H NMR (200 MHz, $CDCl_3$) δ ppm 5.85–5.72 (1 H, m), 5.20–5.12 (2 H, m), 4.39–4.29 (2 H, m), 4.01–3.95 (1 H, m), 2.60–2.54 (1 H, m), 2.49–2.30 (2 H, m), 0.88 (9 H, s), 0.08 (3 H, s) and 0.06 (3 H, s).
  ii) the title compound (746 mg, 2.9 mmol, 7%).

EXAMPLE 10

(3S, 4R)-3-Allyl-4-(tert-butyldimethylsilyloxy) Tetrahydrofuran-2-ol

The lactone of Example 9 (5.0 g, 19.50 mmol) was dissolved in dry toluene (50 ml) and cooled to −70° C. under nitrogen. Diisobutylaluminium hydride (1.5M, 19.5 ml, 29.25 mmol) was added over 15 mins (temperature was maintained below −60° C.) and the resulting mixture was stirred for 1.5 h. The reaction was quenched with methanol (5 ml) (vigorous frothing initially). Aqueous sulfuric acid (2N, 75 ml) was added, maintaining the temperature below −30° C. The mixture was allowed to warm to room temperature and the organic layer was separated. The aqueous phase was extracted with toluene (50 ml +25 ml) (the second extract contained no product). The combined organic solutions were washed with aqueous sulfuric acid (2N, 25 ml), water (3×30 ml, to pH 7) and brine (30 ml). The solution was dried ($MgSO_4$), filtered and evaporated to give the lactol as a colourless oil (5.18 g, 20.04 mmol, 103%), 1.5:1 mixture anomers; $^1$H NMR(200 MHz, $CDCl_3$) δ ppm 5.95–5.80 (1 H, m, both anomers), 5.30–5.00 (3 H, m, both anomers), 4.46–4.41 (1 H, m, major), 4.30 (1 H, t, J 3.5, minor), 4.16–4.03 (1 H, m, both anomers), 3.90 (1 H, dd, J 9, 3, minor), 3.82–3.69 (1 H, m, both anomers), 3.50 (1 H, br, major), 2.42–1.97 (3 H, m, both anomers), 0.92 (9H, s, both anomers), 0.10 (3 H, s, both anomers) and 0.06 (3 H, s, both anomers).

EXAMPLE 11

(3S,4R)-3-Allyl-4-(tert-butyldimethylsilyloxy)-2-trimethylsilyloxytetrahydrofuran The lactol of Example 10 (5.03 g, 19.50 mmol) was dissolved in dry tetrahydrofuran (50 ml) under nitrogen and the solution was cooled to 5° C. in an ice-bath. Triethylamine (4.0 ml, 29.25 mmol) was added, followed by trimethylsilyl chloride (2.60 ml, 20.47 mmol) dropwise over 2 minutes (internal temperature rose to 7° C.). The mixture was stirred for 45 minutes, then allowed to warm to room temperature and stirred for a further 75 minutes (TLC MTBE/heptane 1:4 showed very little lactol). The reaction was quenched with water (50 ml) and extracted with heptane (2×50 ml). The organic extracts were washed with brine (30 ml), dried (MgSO$_4$), filtered and evaporated. The residue was filtered through a pad of silica, eluting with 5% MTBE in heptane (150 ml) to give the silyl acetal as a colourless oil (6.30 g, 19.05 mmol, 98%) approx 5:1 mixture of anomers; Found: C, 58.4; H, 10.35. C$_{16}$H$_{34}$O$_3$Si$_2$ requires C, 58.1; H 10.4%; v$_{max}$ (film) 1641 cm$^{-1}$, [α] +65.1° (c=1.0, CH$_2$Cl$_2$); $^1$H NMR (400 MHz, CDCl$_3$) δ ppm (major anomer) 5.90–5.73 (1 H, m), 5.20–5.00 (3 H, m), 4.48–4.42 (1 H, m), 4.09 (1 H, dd, J 9, 4.5), 3.67 (1 H, dd, J 9, 3), 2.40–2.27 (1 H, m), 2.15–2.00 (2 H, m), 0.91 (9 H, s), 0.16–0.00 (15 H, m); m/z (GCMS, EI) 273 (M-$^t$Bu, 1%) and 117 (100).

EXAMPLE 12

[2R,(1E,3R),3R,4R]3-Allyl-4-tert-butyldimethylsilyloxy-2-[3-tert-butyldimethyl-silyloxy-4-(3-chlorophenoxy)-1-butenyl]-tetrahydrofuran Dry ether (20 ml) and tert-butyllithium (1.5 M, 22.8 ml, 34.3 mmol) were added to a 250 ml 3-necked flask at −70° C. under nitrogen. A solution of the vinyl iodide (E)1-iodo-4-(3-chlorophenoxy)-3(R)-tert-butyldimethylsilyloxy-1-butene (8.16 g, 18.6 mmol) in ether (30 ml) was added over 40 minutes (the internal temperature was maintained at −60 to −70° C., yellow solution initially which slowly darkens to orange/brown). The solution was stirred for a further 40 minutes after complete addition.

The silyl acetal of Example 11 (4.73 g, 14.3 mmol) was dissolved in dry dichloromethane (35 ml) and cooled to −60° C. under nitrogen. Trimethylsilyl bromide (1.85 ml, 14.3 mmol) was added and the mixture was stirred for 1 h, maintaining the temperature below −60° C.

n-Butyllithium (2.5 M, 7.4 ml, 18.6 mmol) was added to thiophene (1.56 g, 18.6 mmol) in dry tetrahydrofuran (15 ml) at −30° C. under nitrogen. The thienyllithium solution was stirred for 20 minutes and then added to a suspension of copper cyanide (1.66 g, 18.6 mmol) in tetrahydrofuran (15 ml) at −20° C. under nitrogen. The mixture was allowed to warm until a clear brown solution was obtained. The lithium 2-thienylcyanocuprate solution was added to the vinyl-lithium solution, keeping the temperature below −60° C. (dark brown solution, some solids present). After 10 minutes, the activated bromoether was added to the cuprate, keeping the temperature below −60° C. (clear yellow/brown solution resulted). After 2 h, TLC (MTBE/heptane 1:15) indicated complete reaction. The reaction was quenched with saturated ammonium chloride solution (100 ml) and allowed to warm to room temperature. The mixture was diluted with water (50 ml) and then filtered through Celite. The organic layer was separated and the Celite was washed with MTBE (100 ml). This washing was also used to extract the aqueous layer. The combined organic phases were washed with water (50 ml), brine (50 ml), dried (MgSO$_4$), filtered and evaporated to give a yellow oil (9.9 g). This was chromatographed (6% MTBE in heptane) to give the tetrahydrofuran (9) as a pale yellow oil (5.02 g, 9.1 mmol, 63%); Found: C, 63.0 ; H, 8.9. C$_{29}$H$_{49}$ClO$_4$Si$_2$ requires C, 62.95; H 8.9%; v$_{max}$ (film) 1595 cm$^{-1}$; [α] +43.9° (c=1.0, CH$_2$Cl$_2$); $^1$H NMR (400 MHz, CDCl$_3$)δ ppm 7.18 (1 H, t, J 8), 6.91 (1 H, d, J 7.5), 6.87 (1 H, t, J 2), 6.76 (1 H, dd, J 8, 2), 5.81–5.78 (3 H, m), 5.08–4.97 (2 H, m), 4.53 (1 H, m), 4.35 (1 H, t, J 4), 4.15 (1 H, m), 4.03 (1 H, dd, J 9, 3.5), 3.84 (2 H, d, J 6), 3.75 (1 H, d, J 9), 2.30 (1 H, m), 2.05 (1 H, m), 1.70(1 H, m), 0.91(18 H, s), 0.09 (6 H, s) and 0.06 (6 H, s); $^{13}$C NMR (100 MHz, CDCl$_3$) δ ppm 159.52, 136.87, 134.80, 132.33, 131.65, 130.16, 120.86, 115.65, 114.92, 112.87, 82.43, 75.73, 73.07, 72.35, 71.10, 50.92, 28.95, 25.80, 18.31, 18.04, −4.35, −4.63, −4.71 and −4.97; m/z (CI) 575 (M$^{35}$Cl +Na, 2%), 421 (48), 156 (69) and 114 (100).

EXAMPLE 13

[2R,(1E,3R),3R,4R]3-{4-tert-butyldimethylsilyloxy-2-[3-tert-butyldimethylsilyloxy-4-(3-chlorophenoxy)but-1-enyl]Tetrahydrofuran-3-yl}-propan-1-ol The 3-allyltetrahydrofuran (9) of Example 12 (2.43 g, 4.39 mmol) was dissolved in dry tetrahydrofuran (25 ml) under nitrogen. 9-Borabicyclo[3.3.1] nonane (0.5M in THF, 10.0 ml, 5 mmol) was added over 5 minutes (a cold water bath was used to maintain the temperature below 20° C.). The mixture was stirred for 2.5 h (TLC, MTBE/heptane 1:3 showed no starting material). The reaction was cooled in a ice bath to 5° C. Sodium hydroxide solution (3M, 2.0 ml) and hydrogen peroxide (27.5%, 2.3 ml) were added in small portions, keeping the temperature below 10° C. (addition of further sodium hydroxide (3M, 0.2 ml) and hydrogen peroxide (27.5%, 0.3 ml) showed no further exotherm). The mixture was warmed to room temperature and stirred for a further 30 minutes. The reaction was poured into water (50 ml) and extracted with MTBE (3×30 ml) [brine (25 ml) was added to aid separation of phases]. The combined organic layers were washed with brine (2×30 ml), dried (MgSO$_4$), filtered and evaporated. The residue was chromatographed (MTBE/heptane 1:4 to 1:2) to give the alcohol as a colourless oil (1.96 g, 3.43 mmol, 78%); Found: C, 60.9; H, 9.0; C$_{29}$H$_{51}$ClO$_5$Si$_2$ requires C, 61.0; H, 9.0%; v$_{max}$ (film) 3446 cm$^{-1}$, [α] +45.1° (c=1.0, CH$_2$Cl$_2$); $^1$H NMR (400 MHz, CDCl$_3$) δ ppm 7.19 (1 H, t, J 8), 6.90 (1 H, t, J 2), 6.86 (1 H, t, J 2), 6.75 (1 H, dd, J 8,2), 5.77 (2 H, m), 4.53 (1 H, m), 4.34 (1 H, m), 4.05 (1 H, m), 4.01 (1 H, dd, J 9,4), 3.86 (2 H, m), 3.76(1 H, d, J 9.5), 3.62 (2 H, m), 1.65–1.4 (4 H, m), 1.25–1.15 (2 H, m), 0.91 (18 H, s), 0.11 (3 H, s), 0.10 (3 H, s), 0.09 (3 H, s) and 0.08 (3 H, s); $^{13}$C NMR (100 MHz, CDCl$_3$) δ ppm 159.51, 134.80, 132.54, 131.78, 130.20, 120.88, 114.95, 112.85, 82.75, 75.81, 73.10, 72.32, 71.01, 63.06,51.11, 31.23,25.82, 25.76,20.66, 18.31, 18.02,−4.28,−4.62, −4.70 and −5.03; m/z (CI) 595 (M$^{37}$Cl+Na, 43%) and 593 (M$^{35}$Cl+Na, 100).

EXAMPLE 14

[2R,(1E,3R),3R,4R]3-{4-tert-butyldimethylsilyloxy-2-[3-tert-butyldimethylsilyloxy-4-(3-chlorophenoxy)but-1-enyl]tetrahydrofuran-3-yl}-propionaldehyde A solution of dry dimethylsulfoxide (0.82 ml, 11.6 mmol) in dry dichloromethane (10 ml) was added over 5 minutes to a solution of oxalyl chloride (2M in dichloromethane, 2.65 ml) in dichloromethane (20 ml) at −60° C. under nitrogen. Stirring was continued for 5 minutes, then a solution of the alcohol of Example 13 (2.76 g, 4.83 mmol) in dichloromethane (15 ml) was added over 5 minutes (maintaining the temperature below −60° C.). The alcohol was washed in with dichloromethane (5 ml) and the reaction was stirred for 40 minutes. Triethylamine (3.4 ml, 24.2 mmol) was added dropwise and after 15 minutes the reaction was allowed to warm to room temperature. Water (50 ml) was added and the mixture was extracted with heptane (2×50 ml). The combined organic phases were washed with hydrochloric acid (1 M, 50 ml), water (50 ml), sodium carbonate solution (5%, 50 ml), water (50 ml) and brine (50 ml), dried (MgSO$_4$), filtered and evaporated. The residue was chromatographed (MTBE/ heptane 1:4) to give the aldehyde (10) (2.55 g, 4.47 mmol, 92%); Found: C, 61.35; H. 8.7. $C_{29}H_{49}ClO_5Si_2$ requires C, 61.2; H, 8.7%, $v_{max}$ (film) 1727 cm$^{-1}$; [α] +47.0° (c =1.0, $CH_2Cl_2$); $^1$HNMR (400 MHz, CDCl$_3$) δ ppm 9.72 (1 H, m), 7.18 (1 H, t, J 8), 6.91(1 H, d, J 8), 6.86 (1 H, t, J 2), 6.75 (1 H, dd, J 8,2), 5.82(2 H, m), 4.53(1 H, m), 4.32(1 H, m), 4.12(1 H, m), 4.04(1 H, dd, J 10, 4), 3.85 (2 H, d, J 6), 3.75 (1 H, d, J 9); 2.44(2 H, m), 1.90(1 H, m), 1.70–1.50(2 H, m), 0.90 (18 H, s), 0.10 (6 H, s) and 0.08 (6 H, s); $^{13}$C NMR (100 MHz, CDCl$_3$) δ ppm 201.67, 159.46, 134.81, 133.03, 131.34, 130.21, 120.91, 114.91, 112.85, 82.71, 75.71, 72.97, 72.27, 71.00, 50.23, 42.19, 25.81, 25.72, 18.29, 17.99, 17.20, −4.26, −4.62, −4.70 and −5.02; m/z (CI) 593 M$^{37}$Cl+Na, 18%), 591 (M$^{35}$Cl+Na, 41) and 114 (100).

EXAMPLE 15

(3-isopropoxycarbonylpropyl)triphenylphosphonium Bromide

Isopropyl 4-bromobutyrate (16.0 g, 76.5 mmol) and triphenylphosphine (20.0 g, 76.5 mmol) in toluene (160 ml) were heated at reflux under nitrogen for 39 h. The mixture was allowed to cool (to approx 40° C.), filtered and the solid was washed with toluene (3 ×25 ml). The product was dried under vacuum to give a white solid (20.7 g, 57%); m.p. 198° C. (onset by DSC); $^1$H NMR (200 MHz, CDCl$_3$) δ ppm 7.85–7.60 (15 H, m), 4.89 (1 H, heptet, J 6), 3.96–3.70 (2 H, m), 2.75 (2 H, t, J 6), 1.95–1.75 (2 H, m) and 1.13 (6 H, d, J 6).

EXAMPLE 16

Isopropyl [2R, (1E, 3R), 3R (4Z), 4R]7-{4-tert-butyldimethylsilyloxy 2-[3-tert-butyl-dimethylsilyloxy-4-(3-chlorophenoxy)but-1-enyl] tetrahydrofuran-3-yl}-hept-4-enoate The phosphonium salt of Example 15 (3.92 g, 8.32 mmol, freshly dried by heating under high vacuum) was suspended in dry tetrahydrofuran (30 ml) and cooled to 0° C. under nitrogen. Potassium bis(trimethylsilyl)amide (0.5 Min toluene, 16.6 ml) was added dropwise over 5 minutes (temperature rose to 3° C.) and the resulting orange solution was stirred for 40 minutes and then cooled to −72° C. A solution of the aldehyde of Example 14 (10) (2.37 g, 4.16 mmol) in tetrahydrofuran (30 ml) was added dropwise over 20 minutes, maintaining the temperature below −70° C. The residues were washed in with tetrahydrofuran (5 ml) and the mixture was stirred for 1.5 h and then allowed to warm to 0° C. over 2 h. The reaction was quenched with saturated ammonium chloride solution (50 ml) (temperature rose to 13° C.) and water (20 ml) to dissolve salts. The organic layer was separated and the aqueous phase was extracted with ethyl acetate (50 ml). The combined organic phases were washed with water (50 ml) and brine (50 ml), dried (Na$_2$SO$_4$), filtered and evaporated. The residue was chromatographed (ethyl acetate/heptane 1:10) to give the silyl protected prostaglandin (2.63 g, 3.88 mmol, 94%); Found: C, 63.45; H, 9.0. $C_{36}H_{61}ClO_6Si_2$ requires C, 63.45; H, 9.0%; $v_{max}$ (film) 1731 cm$^{-1}$, [α] +23.90° (c=1.0, $CH_2Cl_2$); $^1$H NMR (400 MHz, CDCl$_3$) δ ppm 7.18 (1 H, t, J 8), 6.91 (1 H, d, J 8), 6.87 (1 H, t, J 2), 6.76 (1 H, dd, J 8, 2), 5.80 (2 H, m), 5.34 (2 H, m), 5.01 (1 H, heptet, J 6), 4.53(1 H, m),4.34(1 H, m),4.10(1H, m),4.02(1 H, dd, J 9,3.5),3.84(2 H, d, J 6), 3.75(1 H, d, J 9), 2.30 (4 H, m), 2.08 (2 H, m), 1.65 (2 H, m), 1.27 (1 H, m), 1.22 (6 H, d, J 6), 0.91 (18 H, s) and 0.08 (12 H, s); $^{13}$C NMR (100 MHz, CDCl$_3$) δ ppm 172.60, 159.54,134.80,132.41,131.76,130.68,130.17, 127.98,120.85,114.92,112.88, 82.65, 75.86,72.98, 72.38, 71.06,67.56,50.74,34.62,25.77,25.59,24.20,22.96,21.87, 18.31, 18.02, −4.26, −4.62, −4.70 and −5.04; m/z (CI) 705 (M$^{37}$Cl+Na, 49%) and 703 (M$^{35}$Cl+Na, 100).

EXAMPLE 17

Isopropyl [2R(1E,3R),3S(4Z),4R)]-7-{tetrahydro-2-[4-(3-chlorophenoxy)-3-hydroxy-1-butenyl]-4-hydroxy-3-furanyl}-4-heptenoate The silyl protected prostaglandin of Example 16 (2.40 g, 3.52 mmol) was dissolved in tetrahydrofuran (15 ml) (internal temperature 18° C.). Tetrabutylammonium fluoride (1M in tetrahydrofuran, 10.5 ml) was added (temperature rose to 20° C. over 3 minutes) and the mixture was stirred at room temperature under nitrogen for 4 h (TLC ethyl acetate/heptane 3:1 indicated complete reaction). Water (50 ml) was added and the mixture was extracted with ethyl acetate (3×30 ml). The combined organic extracts were washed with water (50 ml) and brine (50 ml), dried (Na$_2$SO$_4$), filtered, and evaporated. The residue was chromatographed (ethyl acetate/heptane 7:3) to give a faintly yellow oil (1.42 g, 3.13 mmol, 89%). The product was passed through a short silica column eluting with neat ethyl acetate to give the 11-oxaprostaglandin (1) as a clear, colourless oil (1.29 g, 2.85 mmol, 81%); $v_{max}$ (film) 3416 and 1725 cm$^{-1}$, [α] +27.6° (c=1.0, EtOH); $^1$H NMR (400 MHz, CDCl$_3$) δ ppm 7.19 (1 H, t, J 8), 6.95 (1 H, d, J 8), 6.91 (1 H, t, J 2), 6.78 (1 H, dd, J 8,2), 5.84 (2 H, m), 5.50–5.30 (2 H, m); 4.99 (1 H, heptet, J 6), 4.56 (1 H, m), 4.41 (1 H, m), 4.14–4.05 (2 H, m), 3.97 (1 H, dd, J 9, 4), 3.93–3.85 (2 H, m), 2.65 (2 H, br), 2.50(1 H, m), 2.36–2.22 (4 H, m), 2.00(1 H, m), 1.75 (1 H, m), 1.52 (1 H, m), 1.43 (1 H, m) and 1.22 (6 H, d, J 6); $^{13}$C NMR (100 MHz, CDCl$_3$) δ ppm 173.15, 159.18, 134.90, 132.71, 130.72, 130.56, 130.29, 128.07, 121.37, 115.09, 113.04, 82.22, 75.46, 72.62, 71.83, 70.14; 67.97, 50.88,34.36,25.81,24.56, 22.70,21.91 and 21.87; m/z (CI) 477 (M$^{37}$Cl+Na, 25%), 475 (M$^{35}$Cl+Na, 69) and 247 (100).

Scheme 1

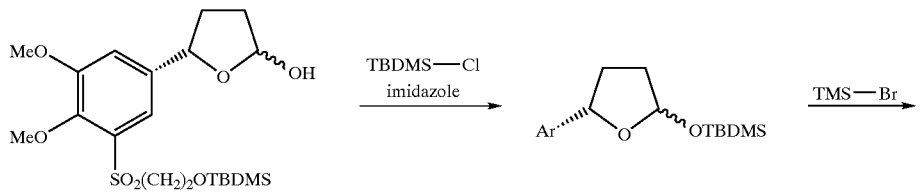

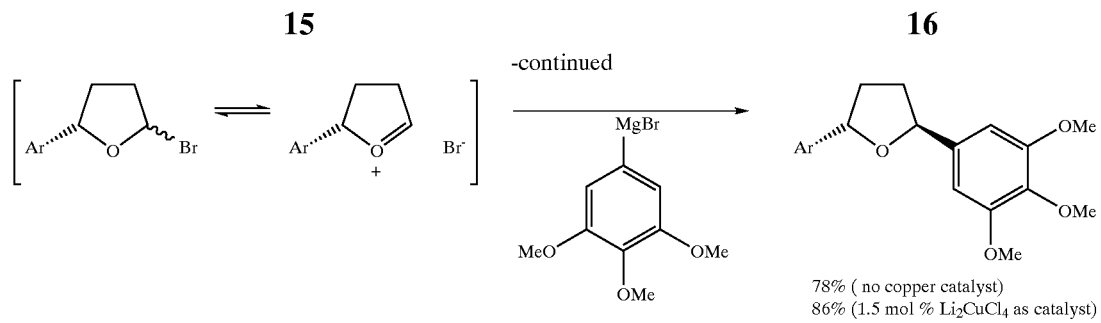

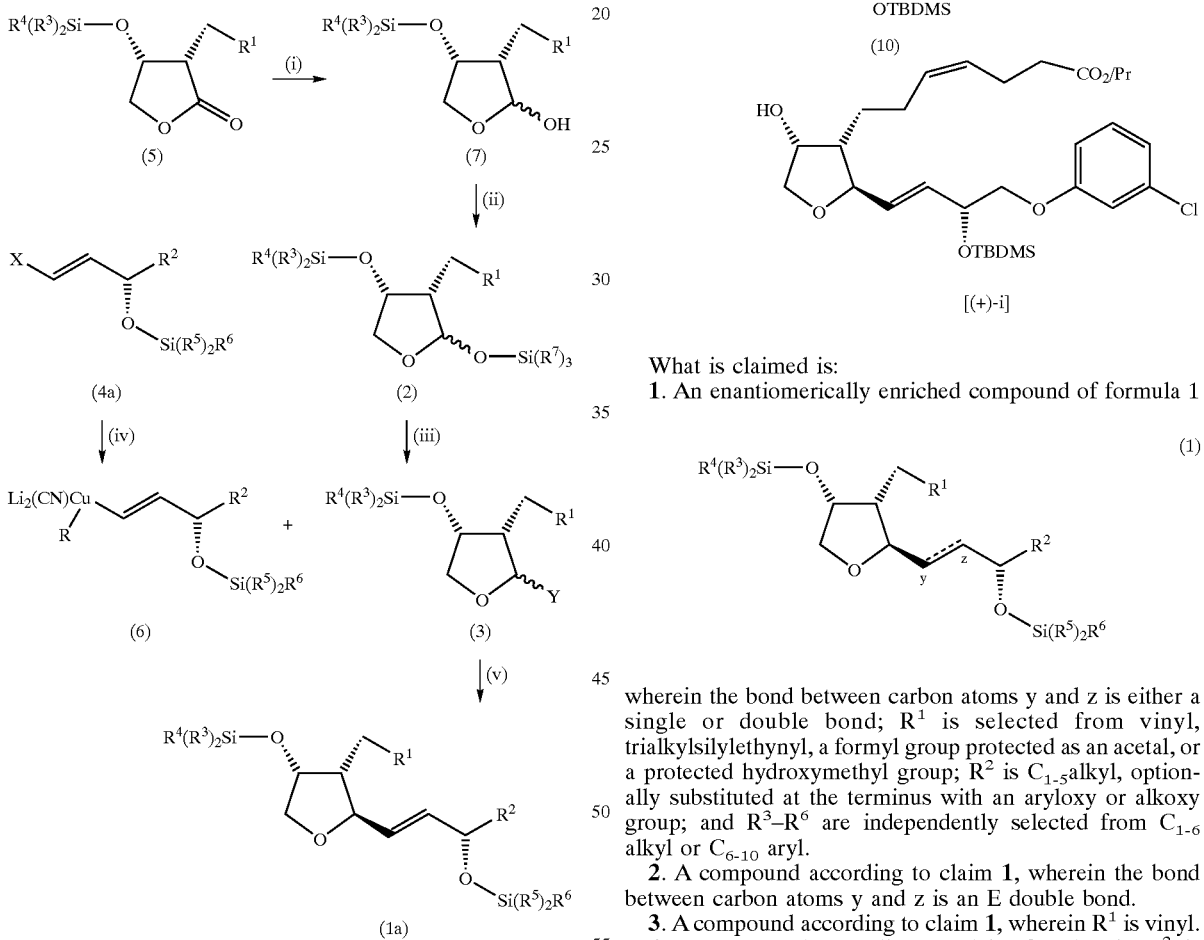

What is claimed is:

1. An enantiomerically enriched compound of formula 1

$$\text{(1)}$$

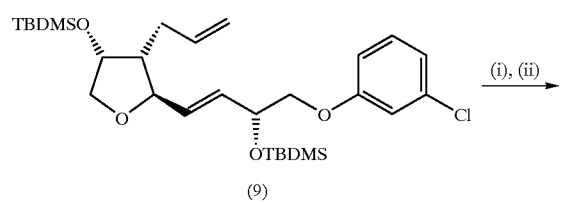

wherein the bond between carbon atoms y and z is either a single or double bond; $R^1$ is selected from vinyl, trialkylsilylethynyl, a formyl group protected as an acetal, or a protected hydroxymethyl group; $R^2$ is $C_{1-5}$alkyl, optionally substituted at the terminus with an aryloxy or alkoxy group; and $R^3$–$R^6$ are independently selected from $C_{1-6}$ alkyl or $C_{6-10}$ aryl.

2. A compound according to claim 1, wherein the bond between carbon atoms y and z is an E double bond.

3. A compound according to claim 1, wherein $R^1$ is vinyl.

4. A compound according to claim 3, wherein $R^2$ is aryloxymethyl.

5. A compound according to claim 4, wherein aryl is 3-chlorophenyl.

6. A compound according to claim 4, wherein $R^3$=$R^5$= methyl and $R^4$=$R^6$=tert-butyl.

7. A compound according to claim 2, wherein $R^1$ is vinyl, $R^2$ is 3-chlorophenoxy methyl, wherein $R^3$=$R^5$=methyl and $R^4$=$R^6$=tert-butyl.

8. A compound according to claim 6, wherein the enantiomeric enrichment is at least 95%.

9. A process for the preparation of a compound of any preceding claim, which comprises the sequential reaction of a silyl acetal of formula 2, wherein $R^7$ is $C_{1-6}$ n-alkyl, with a trimethylsilyl bromide or iodide, and an organometallic derivative of an alkenyl or alkyl halide of formula 4, wherein X is a halide

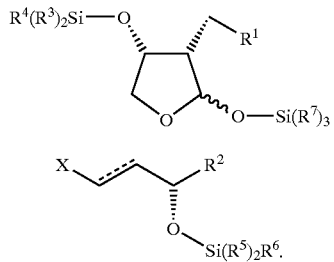

(2)

(4)

10. A process according to claim 9, wherein the organometallic derivative is an alkenyl cuprate.

11. A process according to claim 9, wherein X is iodide.

12. A process according to any of claim 9, wherein $R^7$ is methyl.

13. A process for the preparation of a silyl acetal of formula 2 from a lactone of formula 5, comprising reduction followed by silylation of the resultant lactol, wherein the 2 is formed in a ratio of at least 4:1 relative to the silylated hydroxyaldehyde 8

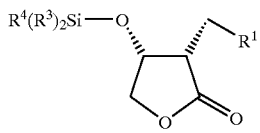

(5)

-continued

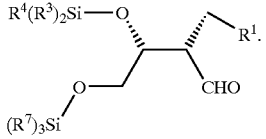

(8)

14. An enantiomerically enriched silyl acetal of formula 2.

15. An enantiomerically enriched lactone of formula 5.

16. A compound according to claim 14 or claim 15, wherein $R^1$ is vinyl.

17. A crystalline lactone of formula 5 according to claim 16, wherein $R^3$ is methyl and $R^4$ is tert-butyl.

18. A process for preparing an 11-oxaprostaglandin comprising the steps of:
 (a) providing a trisubstituted tetrahydrofuran according to claim 1;
 (b) hydroborate the double bond of the trisubstituted tetrahydroforan's allyl substituent to a primary alcohol with a borane;
 (c) oxidate the primary alcohol to an aldehyde;
 (d) react the aldehyde with an ylide to create an alkene; and
 (e) react the alkene with tetra n-butylammonium fluoride to yield 11-oxaprostaglandin (+)-i.

19. The process of claim 18, wherein the 11-oxaprostaglandin is of formula (+)-i:

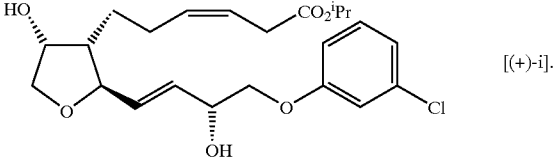

[(+)-i].

* * * * *